United States Patent [19]
Jones et al.

[11] Patent Number: 6,063,761
[45] Date of Patent: May 16, 2000

[54] HEPATOSELECTIVE PHARMACEUTICAL ACTIVES

[75] Inventors: Richard Henry Jones; Fariba Shojaee-Moradi; Peter Henri Sonksen, all of London, United Kingdom; Dietrich Brandenburg; Achim Schuttler, both of Aachen, Germany; Heike Eckey, Holzminden-Silberborn, Germany

[73] Assignees: Kings College London, London, United Kingdom; Deutsches Wollforschuncsinstitut an der Rwth Aachen, Aachen, Germany

[21] Appl. No.: 09/097,535

[22] Filed: Jun. 15, 1998

Related U.S. Application Data

[62] Division of application No. 08/596,285, filed as application No. PCT/GB94/01784, Aug. 15, 1994, Pat. No. 5,854,208.

[30] Foreign Application Priority Data

Aug. 13, 1993 [GB] United Kingdom .................. 9316895

[51] Int. Cl.$^7$ ........................... A61K 38/28; A61K 31/27
[52] U.S. Cl. ................................ 514/3; 514/484; 514/866
[58] Field of Search ................................ 514/3, 484, 866

[56] References Cited

U.S. PATENT DOCUMENTS 5,268,453 12/1993 Andy et al. ............................. 530/303
5,854,208 12/1998 Jones et al. .

FOREIGN PATENT DOCUMENTS 0242416 10/1987 European Pat. Off. .
9012814 11/1990 WIPO .
9112817 9/1991 WIPO .
9200322 1/1992 WIPO .
9215611 9/1992 WIPO .
9507931 3/1995 WIPO .

OTHER PUBLICATIONS

Windhoz et al. The Merck Index, 10$^{th}$, p. 723 abstract No. 4866.
Chemical Abstracts (99:116795m) Kaliman et al. (1983).
J. Brange et al., Diabetes Care, vol. 13, No. 9 "Monomeric Insulins and Their Experimental and Clinical Implications" Sep. 9, 1990, pp. 923–925.
Ronald S. Spangler, "Selective insulinization of liver in conscious diabetic dogs", Am. J. Physiol. 249 (Endocrinal. Metab. 12) pp. E152–159 (1985).
J. Markussen et al., Soluble, fatty acid acylated insulins bind to albumin and show protracted action in pigs, No. 262, pp. 002–009.
Journal of Controlled Release, (1992), pp. 179–188, Trials of Lipid modification of piptide hormones for intestinal delivery.
Pharmaceutical Research, vol. 6, No. 2, (1989), Synthesis of Palmitoyl Derivatives of Insulin and Their Biological Activities.
Proceedings of the Second International Insulin Symposium Aachen, Germany, Sep. 4–7, 1979, Insulin Chemistry, Structure and Function of Insulin and Related Hormones.
F. Shojaee–Moradi, et al., "Convalent Insulin Dimers Are Hepatoselective", Abstract, Medical and Scientific Section, Apr. 13–15, 1989.
Snyder, S. M. et al. "The Binding of Thyroid Hormone Analogues to Thyrozine–Binding Globulin (TBG)", in Thyroid Research (Robbin J. and Braverman L. E. eds.) (1976) pp. 297 to 299.
Snyder, S. M. et al. (1976) Binding of Thyroid Hormones and their Analogues to Thyroxin–Binding Globulin in Human Serum, J. Biol. Chem. 251 (21), 6489 to 6494.
Robbins, J. et al. "Plasma Transport of Thyroid Hormones" from Thyroid Hormone Metabolism (Hennemann, G. ed) 1986, 3 to 38.

*Primary Examiner*—Kevin E. Weddington
*Attorney, Agent, or Firm*—Sughrue, Mion, Zinn, Macpeak & Seas, PLLC

[57] ABSTRACT

The invention provides an analogue of a pharmaceutical active whose molecular weight is less than 25,000 Daltons, the analogue comprising a pharmaceutical active whose molecular weight is less than 25,000 Daltons covalently linked to a pendant molecular group wherein as a result of the administration of the composition to the human or animal body an active complex having a molecular weight of 25,000 Daltons or greater is present in the human or animal circulatory system. The analogue is hepatoselective when administered to the circulatory system. Preferably the analogue is an insulin analogue comprising an insulin or functional equivalent thereof covalently linked to the pendant molecular group wherein the active complex is an insulin complex. Such an insulin analogue may be used in a method of insulin replacement therapy.

17 Claims, No Drawings

HEPATOSELECTIVE PHARMACEUTICAL ACTIVES

This application is a divisional of Ser. No. 08/596,285 filed Feb. 13, 1996: U.S. Pat. No. 5,854,208 which is a 371 of PCT/GB94/01784 filed Aug. 15, 1994.

The present invention relates to novel hepatoselective pharmaceutical actives. In particular it relates to novel hepatoselective insulin analogues suitable for use in an improved treatment of diabetes mellitus.

When drugs and other pharmaceutical actives are administered to the human or animal body it may be required that the active is needed to be present primarily in the liver or to act primarily on the tissues of the liver. That is, the active is required to be hepatoselective. Achieving hepatoselectivity can be difficult, in particular where the active is administered by injection into the skin. One case in which achievement of hepatoselectivity would be especially desirable is the administration of insulin.

The hormone insulin, secreted by the pancreas, has various important roles to play in glucose metabolism. In the liver, after binding to cell surface receptors, insulin promotes the conversion of glucose to glycogen (glycogenesis), promotes protein synthesis and inhibits fat breakdown. Insulin deficiency results in breakdown of glycogen (glycogenolysis), protein and conversion of products of fat and protein breakdown to glucose (gluconeogenesis) leading to a raised plasma glucose level (hyperglycaemia). In subjects who produce adequate amounts of insulin the blood glucose level remains within a certain range. Any excess of glucose is stored in the liver and muscles as glycogen.

Insulin also acts on cell membrane receptors in other tissues to enhance the entry of glucose into cells, thereby diminishing the plasma glucose concentration.

Thus insulin acts to reduce the plasma glucose level by reducing the production of glucose by the liver and by increasing uptake and metabolism of glucose by the liver and by increasing uptake and metabolism of glucose by peripheral tissues.

Deficiency of insulin due to disease of the islets of Langerhans and/or deficiency of insulin action results in diabetes mellitus, a condition in which the blood glucose concentration is high.

In subjects who are not diabetic insulin is produced in the pancreas and transported directly to the hepatic circulation and hence is transported to the liver before any other organs or regions of the body. Thus the liver experiences a very high exposure to the insulin produced. Usually at least 50% of the insulin produced is bound to receptors in the liver, and hence acts in the liver. Insulin bound to receptors in the liver is removed from the circulation and degraded by the liver cells. The insulin which is not bound in the liver and hence passes to the peripheral circulation is therefore at a much lover concentration. Thus the peripheral tissues (eg fat and muscle) which are also targets of the insulin experience a smaller exposure to the insulin secreted.

In diabetic subjects treatment is often carried out by insulin-replacement therapy. In general an insulin preparation is injected subcutaneously. The most common subcutaneous insulin regimen involves twice-daily injection of mixtures of short- and intermediate-acting insulin preparations. Insulin is absorbed from the subcutis into the peripheral circulation and thence to the entire body, including the liver. With such a system the liver and the peripheral tissues tend to experience approximately equal exposure to insulin.

There are various disadvantages and negative side-effects with the use of this system.

First, if sufficient insulin is injected to enable a high enough concentration to be present in the hepatic circulation then too high a concentration will be present in the peripheral circulation. Similarly if a suitable concentration is present in the peripheral circulation the concentration of insulin in the hepatic circulation will be inadequate.

There is believed to be a danger associated with high concentrations of insulin in the peripheral circulation (hyperinsulinaemia) of cardiovascular disease.

Second, there is a serious risk of hypoglycaeaia in diabetic subjects receiving insulin replacement therapy by subcutaneous injection. A concentration of insulin in the peripheral circulation which is too high can lead to a blood sugar level which is too low and subsequent collapse.

It would therefore be desirable to be able to direct a large concentration of insulin directly to the hepatic insulin receptors with a lower concentration of insulin being directed to the peripheral insulin receptors. It would also be desirable to achieve such hepatoselectivity for other active molecules.

Some attempts have been made to obtain the desired hepatoselectivity of insulin. Intravenous injection directly into the hepatic portal circulation could allow injected insulin to pass directly to the liver before reaching the peripheral circulation. Such a system is unsuitable for general use due to the difficulty and complicated nature of its operation; in particular it is not suitable for use by diabetic patients themselves except under exceptional circumstances.

An attempt has been made to render insulin hepatoselective by injecting it subcutaneously whilst encapsulated in lipid vesicles. (Spangler, Ronald S., "Selective Insulinisation of Liver in Conscious Diabetic Dogs", Am. J. Physiol. 249 (Endocrinol. Metab. 12) : E152–E159, 1985). Insulin encapsulated in lipid vesicles (designated vesicle encapsulated insulin VEI) was targeted to hepatocytes by means of a digalactosyl diglyceride moiety incorporated on the outside of the lipid vesicles. Using this approach it was possible to alter the distribution of an administered glucose load to favour hepatic deposition.

The present inventors have found (British Diabetic Association Medical and Scientific section Conference, Manchester, Apr. 13–15, 1989) that covalent dimers of insulin (molecular weight ±12,000 Daltons rather than ±6,000 for insulin monomer) have a greater effect on hepatic glucose output than on peripheral uptake and utilisation. That is, the covalent insulin dimers appear to act preferentially on hepatocytes rather than on cells of the peripheral tissues. It has also been found that proinsulin shows this hepatoslectivity to a smaller degree. Proinsulin is the zymogen which is cleaved to form the active hormone insulin. The proinsulin molecule is larger than the active insulin molecule.

The cells of the peripheral tissues, for instance fat and muscle, are separated from the blood vessels by the capillary endothelium. In the liver however there is no such barrier between blood vessels and hepatocytes.

It is thought that transport across the capillary endothelium is mainly by diffusion i.e. active transport of insulin across the capillary endothelium does not occur to any significant extent. Therefore the present inventors believe that the absorption of insulin into the peripheral tissues is determined by factors influencing diffusive transport, in particular by steric hindrance or size of molecules. This is believed to be a reason for the relative hepatoselectivity of covalent insulin dimers and proinsulin when compared with insulin monomers; both have free access to hepatocytes but the larger covalent insulin dimer or proinsulin is absorbed into the peripheral tissues from the bloodstream more slowly than is the insulin monomer. Thus the larger molecules spend a longer time in the bloodstream before being absorbed into the peripheral tissues and are thus are more likely to reach the liver, where they may be active more easily.

According to the present invention there is provided the use of an analogue of a pharmaceutical active whose molecular weight is less than 25,000 Daltons in the manufacture of a composition for use in a method of treatment of the human or animal body, the analogue comprising a pharmaceutical active whose molecular weight is less than 25,000 Daltons covalently linked to a pendant molecular group wherein as a result of the administration of the composition to the human or animal body an active complex having a molecular weight of 25,000 Daltons or greater is present in the human or animal circulatory system.

The invention is of particular usefulness when the analogue is an insulin analogue which comprises an insulin or functional equivalent thereof covalently linked to a pendant molecular group, so that as a result of the administration of the composition to the human or animal body an insulin complex having a molecular weight of 25,000 Daltons or greater is present in the human or animal circulatory system. This invention is also applicable to other pharmaceutical actives of molecular weight below 25,000 Daltons which are administered so as to enter the circulatory system and which are required to be hepatoselective and for which similar problems as those encountered with the administration of insulin therefore also apply. In this specification the invention is discussed primarily in terms of its use for giving hepatoselectivity to insulin or a functional equivalent thereof, but it will be understood that the disclosures made are equally applicable to other pharmaceutical actives of molecular weight less than 25,000 Daltons.

According to a first, particularly preferred, embodiment of the invention the pendant molecular group has an affinity for one or more binding proteins present in the human or animal circulatory system wherein the total molecular weight of the insulin or functional equivalent thereof (or other pharmaceutical active) and the additional molecular group and the one or more binding proteins is 25,000 Daltons or greater.

Binding proteins "in the human or animal circulatory system" are those which are present in the blood plasma.

Thus when the analogue is introduced into the bloodstream the one or more binding proteins will become non-covalently linked to the additional molecular group, forming a complex which has a molecular weight of 25,000 Daltons or greater.

According to a second embodiment of the invention an insulin analogue (or analogue of another pharmaceutical active) is used which additionally comprises one or more binding proteins non-covalently attached to the pendant molecular group wherein the total molecular weight of the insulin or functional equivalent thereof (or other pharmaceutical active) and the pendant molecular group and the one or more binding proteins is 25,000 or greater.

In this second embodiment the analogue is a complex having a molecular weight of 25,000 or greater and may be administered into the circulatory system as such, for instance intravenously.

According to a third embodiment of the invention an insulin analogue (or analogue of other pharmaceutical active) is used in which the total molecular weight of the insulin or functional equivalent thereof (or other pharmaceutical active) and the covalently linked pendant molecular group is 25,000 Daltons or greater.

As with the second embodiment, the analogue is a complex having a molecular weight of 25,000 or greater and may be administered into the circulatory system as such, for instance intravenously.

For use in the first aspect of the present invention there is provided an analogue of a pharmaceutical active whose molecular weight is less than 25,000 Daltons comprising a pharmaceutical active whose molecular weight is less than 25,000 Daltons covalently linked to a pendant molecular group, said pendant molecular group having an affinity for one or more binding proteins present in the human or animal circulatory system.

As explained above, the invention is especially useful when the compound is an insulin analogue comprising an insulin or functional equivalent thereof covalently linked to a pendant molecular group which has an affinity for one or more binding proteins present in the human or animal circulatory system.

Such an insulin analogue (or analogue of other pharmaceutical active) may be injected subcutaneously and absorbed into the bloodstream through the capillary endothelium without difficulty. When in the bloodstream the insulin analogue will come into contact with the binding protein for which the covalently-linked pendant molecular group has an affinity. Thus at least some molecules of the insulin analogue will become bound to the said binding protein, forming an insulin complex. Binding proteins tend to be bulky molecules of high molecular weight. They therefore tend not to diffuse out through the capillary endothelium easily and remain in the bloodstream. Thus the effective size of molecule and hence the molecular weight of the bound insulin analogue is increased dramatically. Absorption from the blood vessels into the peripheral tissues, for instance fat and muscle, through the capillary endothelium is now greatly inhibited due to the attachment of the insulin analogue to the high molecular weight binding protein. In the liver however there is no such barrier therefore the insulin analogue even with the associated binding protein may have access to the hepatocyte insulin receptors essentially to the same degree as would conventional insulin.

In the same way an analogue of another pharmaceutical active may be induced not to diffuse out through the capillary endothelium and to remain in the bloodstream until it is carried to the liver where it may act or be taken up as required.

Binding of the pendant molecular group and the binding protein is not covalent. Binding forces may be for instance electrostatic (eg attraction of opposite charges, hydrogen bonding) or hydrophobic. Thus binding is not permanent. The insulin analogue (or analogue of other pharmaceutical active) may be absorbed onto the hepatic tissues in its bound form. Molecules of the insulin analogue which have not been bound by the binding protein or which have become bound and subsequently unbound are capable of passing through the capillary endothelium into the peripheral tissues.

The covalently-linked molecular group is attached in such a way that the active site (or sites) of the insulin equivalent or other pharmaceutical active remains available to carry out its prescribed functions.

Attachment of a suitable molecular group to the insulin equivalent (or other active) may be carried out by conventional chemical methods known to those skilled in the art.

According to this aspect of the invention there is also provided a method of insulin replacement therapy comprising subcutaneous injection of a preparation comprising an insulin analogue as described above.

Preferred features of the first embodiment of the invention will now be described in detail.

The insulin or functional equivalent thereof, when, insulin is the active used, may be any of the insulins conventionally used in insulin replacement therapy.

J. Brange et al ("Monomeric Insulins and their Experimental and Clinical Implications", Diabetes Care, vol. 13, no. 9, September 1990) and others have studied the possibility of developing insulins with reduced tendencies to self-association. These insulins are absorbed from the subcutis into the bloodstream more rapidly than is the form in which insulin is usually found in pharmaceutical formulations. Insulin assumes an associated state in pharmaceutical formulation. Six monomers of insulin associate to form hexamers. The association is non-covalent. With the use of DNA technology Brange et al and others have prepared insulins which remain dimeric or even monomeric at high (pharmaceutical) concentration by the introduction of one or a few amino acid substitutions into human insulin. Insulins with reduced association capacity as described by Brange et al and others are preferred for use as the insulin equivalent to which the additional molecular group is attached. When the pharmaceutical active is an insulin equivalent such insulins are preferred, because their reduced tendency to self-associate means that they are more rapidly absorbed into the bloodstream from the subcutis than are conventional insulins which tend to be injected in hexameric form.

Insulins of this type have also been developed by Eli Lilly. These are described in Protein Engineering, Vol 5, 519–525 and 527–533 (1992) (both D. N. Brems et al). Studies of amino acid modified monomeric insulins have also been described in Diabetes 40 Suppl. 1 (1991), 423A (Howey et al) and 464A (Shaw et al).

The pendant molecular group covalently linked to the insulin equivalent or other active may be any molecular group which has an affinity for a binding protein present in the circulatory system and which will not itself act in the body to give detrimental effects. The molecular group chosen should usually be of a molecular weight similar to or less than that of the insulin equivalent or other active. Preferably the total molecular weight of the insulin or functional equivalent thereof or other active and the additional molecular group is less than 25,000, more preferably less than 20,000 or 15,000, and may be less than 12,000. This is in order that attachment of the pendant molecular group to the insulin equivalent or other active to form the analogue should not hinder the passage by diffusion of the injected analogue from the subcutis through the capillary endothelium into the bloodstream. Preferred molecular groups are molecular structures which possess an affinity for one or more proteins which are naturally present in the circulation. They may be based on naturally-occurring hormones or on functional equivalents of such hormones which also possess affinity to their binding proteins or they may be based on other substances for which such binding proteins exist. The pendant molecular group should be harmless when injected into the body; this may be achieved for instance by ensuring that the concentration of insulin analogue or analogue of other active in the bloodstream is high enough to allow the beneficial effects of insulin or other therapy to be felt, but low enough to prevent any effects which might be due to the pendant molecular group being felt, or by ensuring that the insulin analogue or analogue of other active is not present in parts of the body where the pendant molecular group might be active, or by rendering the pendant molecular group inactive by structural modification which nevertheless preserves its ability to bind to its binding protein.

The pendant molecular group may be itself an insulin equivalent, for instance insulin-like growth factor 1 (IGF1). This polypeptide has an affinity for IGF1 binding proteins, which circulate naturally in the human bloodstream.

The pendant molecular group may be a native or modified thyroxyl group, derived from the human thyroid hormone thyroxine 3,5,3',5'-L-tetraiodothyronine (T4). There are several binding proteins present in the human circulatory system which have an affinity for the T4 group, for instance thyroxine binding globulin (TBG), thyroxine binding prealbumin (TBPA) and albumin. These proteins are known collectively as thyroxine binding proteins (TBP).

Other suitable groups derived from hormones or their functional equivalents may be used. Suitable groups may be ascertained by a skilled person using methods known in the pharmaceutical field.

The pendant molecular group with an affinity for a binding protein may be covalently attached directly to the insulin equivalent (or other active), as explained above in a place chosen so that the additional molecular group does not inhibit the action of the insulin equivalent. The structure of insulin and the locations of its active sites are well known, therefore when insulin is used those skilled in the art will be able to establish appropriate positions at which to attach the said molecular group so as not to interfere significantly with the action of the insulin or equivalent.

Alternatively a short molecular chain (or "spacer arm") may be used to link the insulin equivalent (or other active) and the said molecular group. The spacer arm is linked covalently both to the insulin equivalent and to the pendant molecular group. Such a spacer arm ensures that the insulin equivalent and binding protein are distanced from one another, thus preventing substantial interference with insulin activity by the (usually bulky) high molecular weight binding protein. The spacer arm is usually a linear chain, preferably of from 3–10 carbon atoms in length. Such a spacer arm may be for instance an aminohexanoyl (AH) group, which is a six-carbon chain. Other groups may of course be used as a spacer arm. For example aminoacids either singly or linked as small peptide sequences could be used.

It should be ensured that the binding protein which has an affinity for the pendant molecular group is present in the blood plasma in sufficiently large amounts that the trapping of the binding protein by the insulin analogue (or analogue of other active) with the covalently linked molecular group will not deplete the levels of binding protein in the blood to detrimental effect. For instance the level of binding protein should not be depleted so that insufficient binding protein is available to carry out its usual function in the body, if any.

The insulin analogue (or analogue of other active) of the invention may be produced by various methods, for instance: chemical reaction of the insulin or insulin equivalent or other active with a substance or substances which include the pendant molecular group; protein synthesis of the complete analogue; production by a genetically engineered micro organism.

The insulin analogue of the invention may be used in a method of insulin replacement therapy.

An insulin analogue according to the invention or a mixture of two or more different insulin analogues according to the invention form part of an insulin preparation. This insulin preparation is suitable for use in a method of treatment of the human or animal body, preferably suitable for subcutaneous injection, and may comprise a treatment for diabetes. Additional ingredients may be added which modify the rate of absorption from the subcutaneous depot into the circulation. The insulin-based preparation preferably is suitable for subcutaneous injection, in which case it is therefore suitable for use by sufferers from diabetes on themselves.

The insulin preparation may comprise the hepatoselective insulin analogue of the invention and a conventional non-hepatoselective insulin. On subcutaneous injection and passing into the bloodstream the conventional insulin will act in the peripheral tissues whilst the insulin analogue of the invention provides a controlled, hepatoselective action.

The analogues of other pharmaceutical actives of the invention may also be used in methods of treatment or therapy by subcutaneous injection of a preparation comprising the analogue of the active.

According to the second embodiment of the invention an insulin analogue (or analogue of other active) with a covalently attached pendant molecular group is used with a binding protein already non-covalently linked to the pendant molecular group. A composition comprising such an insulin analogue would be more suitable for intravenous administration than for subcutaneous administration due to the very high molecular weight of the insulin analogue in the composition (as compared with the insulin analogue of the first embodiment, which forms an insulin complex of molecular weight greater than 25,000 only after administration into the circulatory system). It may be desirable in some cases however to provide such an insulin analogue or analogue of other active for use in the manufacture of a composition suitable for intravenous administration.

The pendant molecular group and binding proteins may be any of those described above as suitable for the first embodiment of the invention. In addition the binding proteins may be proteins which do not occur naturally in the human or animal circulatory system (and which are harmless when introduced into the circulatory system) and the pendant molecular group may be any group with an affinity to such a protein.

According to a third embodiment of the invention an insulin analogue (or analogue of other active) is used which comprises an insulin or functional equivalent thereof (or other active) with a large group covalently attached. Such a group should be large enough that the entire insulin analogue has a molecular weight of at least 25,000. It should also, like the pendant molecular group of the first embodiment of the invention, be harmless when introduced into the body. This may be achieved as described above for the pendant molecular group. The large molecular group of the third embodiment of the invention may for instance be based on a polypeptide structure or on other suitable polymeric structures.

The analogues of the second and third embodiments of the invention may be produced by the methods mentioned above as suitable for the production of the analogue of the first embodiment of the invention. For instance suitable methods in the case of the analogue of the third embodiment include chemical reaction of the insulin or equivalent or other active with a substance or substances which include the covalently linked molecular group, protein synthesis of the complete analogue and production by a genetically engineered micro organism. In the case of the second embodiment the section of the analogue comprising the insulin or equivalent or other active and the additional molecular group may be synthesized in the same way as may be the analogue of the first embodiment. The binding protein may be synthesized for instance by protein synthesis, production by a genetically engineered micro organism, extraction from a naturally-occurring organism. Non-covalent attachment of the binding protein or proteins to the pendant molecular group may be achieved by methods known in the art.

The analogues of the second and third aspects of the invention are suitable for incorporation in compositions which are to be administered intravenously. Where the active is insulin or a functional equivalent thereof, such compositions may be used in a method of insulin replacement therapy. Such compositions comprise one or more insulin analogues of the second and third embodiments of the invention. The composition may also comprise additional ingredients which may be chosen by those skilled in the art.

EXAMPLES

The present inventors have undertaken a study to explore the possibility that insulin analogues with restricted access to peripheral tissues may display relative hepatoselectivity in vivo.

Analogues of insulin which include a thyroxyl moiety which binds to thyroid hormone binding protein (TBP) have been designed and tested. $N^{\alpha B1}$-thyroxyl-insulin (T4-Ins) and $N^{\alpha B1}$-thyroxyl-aminohexanoyl insulin (T4-AH-Ins) were synthesized using methods of chemical synthesis given below.

Preparation of thyroxyl insulins

Abbreviations:

Msc=methylsulphonylethyloxycarbonyl

Boc=tert.butyloxycarbonyl

DMF=dimethylformamide

DMSO=dimethylsulfoxide mp=melting point

ONSU=N-oxysuccinimide ester

Example 1

B1-thyroxyl-insulin (porcine) (T4-Ins)

Protected thyroxine derivatives:

Msc-L-thyroxine (I)

776 mg (1 mmol) L-thyroxine in 2 ml dimethylsulfoxide was reacted with 530 mg (2 mmol) Msc-ONSu in the presence of 139 μl (1 mmol) triethylamine at room temperature for 18 hours. After concentration in vacuo the oily residue was taken up in ethyl acetate, the organic layer washed with water, dried over $Na_2SO_4$, and the solvent removed in vacuo. The solid residue was crystallised from hexane.

Yield: 651 mg (70.2% of theory), mp: 200° C.

Msc-L-thyroxine-N-oxysuccinimide ester (II)

To a cooled (0° C.) solution of 371 mg (0.4 mmol) of Msc-thyroxine and 40 mg (0.4 mmol) N-hydroxysuccinimide in 1 ml tetrahydrofurane a precooled solution of 82.5 mg N,N'-dicyclohexycarbodiimide in 0.5 ml tetrahydrofurane was added under stirring. After further stirring for 3 hours the precipitate was removed by filtration, and the filtrate concentrated in vacuo. Crystallisation of the solid residue from methylenechloride/petroleum ether.

Yield: 295 mg (71%, based on I)

mp: 180° C.

B1-thyroxyl-insulin (porcine) (III)

To a solution of 100 mg (approx 0.016 mmol) A1,B29-$Msc_2$-insulin (prepared according to Schüttler and Brandenburg, Hoppe-Seyler's Z. Physiol, Chem. 360, 1721–1725 (1979)) and 18 μl (0.160 mmol) N-methylmorpholine in 2 ml of DMSO 116.4 ml (0.160 mmol) of II in 0.2 ml DMSO were added. After stirring for 6 h at room temperature the insulin derivative was precipitated with ether/methanol (9:1, v/v), isolated by centrifugation, washed 3 times with ether/methanol, and dried in vacuo.

Msc groups were removed by treatment with NaOH/dioxane/methanol at 0° C., and III was purified by gel filtration on Sephadex G 50 fine as described (Geiger et al, Chem. Ber. 108, 2758–2763 (1975)). Lyophilization gave 78.4 mg B1-thyroxyl-insulin (75%, based on $Msc_2$-insulin).

Example 2

B1-thyroxyl-aminohexanol-insulin (porcine) (IV) (T4-AH-Ins)

1. BOC-ε-aminohexanoic acid was prepared by reacting 1.32 g (10 mmol) ε-aminohexanoic acid with 2.4 g (11 mmol) di-tert.butyldicarbonate in dioxane/water at pH 9 and was obtained in 87% yield (2.2 g). Mp after recrystallization from ethyl acetate: 75° C.

2. 22.8 mg (0.096 mmol) Boc-aminohexanoic acid was preactivated with 13 mg 1-hydroxybenzotriazole and 17.8 mg (0.09 mmol) dicyclohexyl carbodiimide in 0.7 ml dimethylformamide for 1 h at 0° C. and 1 further hour at room temperature.

3. Then, a solution of 100 mg (approx. 0.016 mol) A1,B29-$Msc_2$-insulin and 18 μl (0.160 mmol) N-methylmorpholine in 1 ml of DMF was added. After stirring for 70 minutes at room temperature the mixtures was filtered, and the insulin derivative was precipitated with ethyl ether/methanol (9:1, v/v), isolated by centrifugation, washed 3 times with ether/methanol, and dried in vacuo.

4. The Boc protecting group was cleaved by treatment of the product with 3 ml trifluoro acetic acid for 1 hour at room temperature. The solution was concentrated in vacuo, the insulin derivative precipitated with ether, isolated, washed with ether, and dried. Yield: 77.8 mg of B1-aminohexyl-A1, B29-$Msc_2$-insulin.

5. 102 mg (0.016 mmol) of this derivative was dissolved in 2 ml dimethylformamide and 18 μl (0.16 mmol) N-methylmorpholine. After addition of 116 mg (0.16 mmol) Msc-thyroxine-N-oxysuccinimide ester in 0.2 ml dimethylformamide the mixture was stirred for 3 hours at room temperature. The protected insulin was isolated by precipitation with methanol/ether and isolated as described above.

6. Msc groups were removed by treatment with NaOH/dioxane/methanol at 0° C., and IV was purified by gel filtration on Sephadex G 50 fine as described (Geiger et al, op. cit.). Lyophilization gave 39.1 mg B1-thyroxylaminohexanoyl-insulin (37%, based on aminohexyl-$Msc_2$-insulin).

T4-Ins, T4-AH-Ins and insulin (Ins) were infused into four anaesthetized beagles with D-$^3$H-3-glucose for measurement of the rates of glucose production (Ra) and glucose disposal (Rd). Euglycaemia and glucose specific activity were maintained by variable infusion of D-glucose with D-$^3$H-3-glucose.

With all three materials glucose Rd was increased and glucose Ra decreased from basal level 2.70±0.19 mg. $kg^{-1}$ $min^{-1}$, (p<0.05). In each experiment insulin-like activity for Ra and Rd was calculated as the area between the basal values of each of these variables and subsequent values plotted graphically against time (AUC). For Ins, T4-Ins and T4-AH-Ins respectively, AUC for Ra values were −431±121, −226±154 and −357±50 (mean±SEM, mg/kg), (no significant differences) and AUC for Rd values were 1142±160, 629±125 and 830±178 mg/kg, both analogues different from Ins p<0.05.

These results indicate that insulin analogues of the invention act to a greater extent on the tissues of the liver than on those of the peripheral regions of the body, such as fat and muscle.

We claim:

1. A method of treating diabetes in a human or an animal, comprising the step of:
   administering a conjugate compound having a molecular weight of less than 25 kD comprised of a pharmaceutically active compound and a pendant molecular moiety which is a naturally occurring hormone or an analogue thereof, wherein the pendant molecular moiety has an affinity for one or more binding proteins naturally present in the circulatory system of a human or an animal whereby the conjugate reaches the systemic circulation of the human or the animal and in the circulation forms a complex having a molecular weight of more than 25 kD with the one or more binding proteins.

2. A treatment method according to claim 1, wherein the pharmaceutically active compound is insulin or a functional equivalent of insulin.

3. A treatment method according to claim 1, wherein the pendant molecular moiety is a thyroid hormone.

4. A treatment method according to claim 3, wherein the thyroid hormone is thyroxine.

5. A treatment method according to claim 1, wherein the pendant molecular moiety is IGF1.

6. A treatment method according to claim 2, wherein the pendant molecular moiety is a thyroid hormone.

7. A treatment method according to claim 6, wherein the thyroid hormone is thyroxine.

8. A treatment method according to claim 1, wherein the pendant molecular moiety is linked to the pharmaceutically active compound by a spacer.

9. A treatment method according to claim 8, wherein the spacer is a linear chain of from 3 to 10 carbon atoms in length.

10. A treatment method according to claim 1, wherein the binding protein is selected from the group consisting of albumin, thyroxine-binding pre-albumin, thyroxine-binding globulin, and combinations of those proteins.

11. A treatment method according to claim 2, wherein the binding protein is selected from the group consisting of albumin, thyroxine-binding pre-albumin, thyroxine-binding globulin, and combinations of those proteins.

12. A method according to claim 7, wherein the binding protein is selected from the group consisting of albumin, thyroxine-binding pre-albumin, thyroxine-binding globulin, and combinations of those proteins.

13. A method of delivering a pharmaceutically active compound to a human or an animal comprising:
   a) covalently bonding to the pharmaceutically active compound a pendant molecular moiety which is a naturally occurring hormone or an analogue thereof to form a conjugate compound which has a molecular weight of less than 25 kD; and
   b) administering the said conjugate compound to a human or an animal whereby the conjugate compound is delivered to the circulatory system of the said human or animal and forms a complex therein with one or more binding proteins naturally present in the said circulatory system, said complex having a molecular weight of more than 25 kD.

14. A method of directing a pharmaceutically active compound selectively to the liver of a human or animal comprising the steps:

a) covalently bonding to the pharmaceutically active compound a pendant molecular moiety which is a naturally occurring hormone or an analogue thereof to form a conjugate compound which has a molecular weight of less than 25 kD; and b) administering the said conjugate compound to a human or an animal whereby the conjugate compound is delivered to the circulatory system of the said human or animal and forms a complex therein with one or more binding proteins naturally present in the said circulatory system, said complex having a molecular weight of more than 25 kD.

15. A method of forming a complex in the systemic circulation of a human or an animal comprising the Steps of:

a) covalently bonding to the pharmaceutically active compound a pendant molecular moiety which is a naturally occurring hormone or an analogue thereof to form a conjugate compound which has a molecular weight of less than 25 kD; and b) administering the said conjugate compound to a human or an animal whereby the conjugate compound is delivered to the circulatory system of the said human or animal and forms a complex therein with one or more binding proteins naturally present in the said circulatory system, said complex having a molecular weight of more than 25 kD.

16. A method according to claim 2 in which the pendant molecular moiety is conjugated at the alpha amino group of the B1 residue of the insulin molecule.

17. A method according to claim 6 wherein the pendant molecular moiety is conjugated at the alpha amino group of the B1 residue of the insulin molecule.

* * * * *